US008481053B2

(12) United States Patent
Pillich et al.

(10) Patent No.: US 8,481,053 B2
(45) Date of Patent: Jul. 9, 2013

(54) COMPOSITIONS AND METHODS FOR TREATING OF MICROBIAL INFECTIONS

(75) Inventors: Jiri Pillich, Brno (CZ); John C. Balcarek, Huntsville, AL (US)

(73) Assignee: Immunology Laboratories, Inc., Birmingham, AL (US)

(*) Notice: Subject to any disclaimer, the term of this patent is extended or adjusted under 35 U.S.C. 154(b) by 0 days.

(21) Appl. No.: 13/221,666

(22) Filed: Aug. 30, 2011

(65) Prior Publication Data

US 2012/0076819 A1 Mar. 29, 2012

Related U.S. Application Data

(63) Continuation of application No. 12/640,157, filed on Dec. 17, 2009, now Pat. No. 8,007,817, which is a continuation of application No. 12/069,569, filed on Feb. 11, 2008, now Pat. No. 7,648,707, which is a continuation of application No. 11/170,972, filed on Jun. 30, 2005, now Pat. No. 7,329,409, which is a continuation of application No. 10/367,213, filed on Feb. 13, 2003, now Pat. No. 6,929,798.

(60) Provisional application No. 60/356,483, filed on Feb. 13, 2002.

(51) Int. Cl.
*A61K 39/085* (2006.01)

(52) U.S. Cl.
USPC ............... 424/243.1; 424/197.11; 424/234.4; 424/243; 424/252.3; 424/320.1

(58) Field of Classification Search
None
See application file for complete search history.

(56) References Cited

U.S. PATENT DOCUMENTS

| | | | |
|---|---|---|---|
| 159,192 A | 1/1875 | Leiter | |
| 3,855,197 A * | 12/1974 | Hirsch et al. | 530/395 |
| 4,485,045 A | 11/1984 | Regen | |
| 4,544,545 A | 10/1985 | Ryan | |
| 4,659,558 A | 4/1987 | Urquhart | |
| 4,668,218 A | 5/1987 | Virtanen | |
| 5,013,556 A | 5/1991 | Woodle | |
| 5,458,135 A | 10/1995 | Patton | |
| 5,514,097 A | 5/1996 | Knauer | |
| 5,643,214 A | 7/1997 | Marshall | |
| 6,027,734 A * | 2/2000 | Briles et al. | 424/244.1 |
| 6,294,177 B1 * | 9/2001 | Fattom | 424/243.1 |
| 6,929,798 B2 | 8/2005 | Pillich | |
| 7,329,409 B2 | 2/2008 | Pillich | |
| 7,648,707 B2 | 1/2010 | Pillich | |
| 8,007,817 B2 | 8/2011 | Pillich | |
| 8,043,624 B2 | 10/2011 | Pillich | |
| 2012/0100178 A1 | 4/2012 | Pillich | |

FOREIGN PATENT DOCUMENTS

| | | |
|---|---|---|
| CA | 2476405 | 2/2003 |
| CA | 2476405 | 8/2003 |
| EP | 0237507 | 2/1987 |
| EP | 0516473 | 5/1992 |
| EP | 03711070.7 | 2/2003 |
| EP | 1487273 | 8/2003 |
| FR | 2550707 | 4/1983 |
| HK | 5102303.3 | 2/2003 |
| HK | 1069739 | 8/2003 |
| JP | 2003-567189 | 2/2003 |
| JP | 4304077 | 8/2003 |
| KR | 2004-7012621 | 2/2003 |
| KR | 10-0965026 | 8/2003 |
| WO | WO 94/08552 | 10/1993 |
| WO | WO 94/06498 | 3/1994 |
| WO | WO 94/16970 | 8/1994 |
| WO | WO 97/38731 | 4/1997 |
| WO | WO 97/25086 | 7/1997 |
| WO | WO 98/35888 | 8/1998 |
| WO | WO 03/067991 | 2/2003 |
| WO | WO 03/067991 | 8/2003 |

OTHER PUBLICATIONS

Callens, et al. Kinetic properties of fructose bisphosphate aldolase from Trypanoso brucei compared to aldolase from rabbit muscle and Staphylococcus aureus, Molec Biochem Parasitology 47(1), pp. 1-9 (1991).

Carneiro CRW, et al. Identification of enolase as a laminin-binding protein on the surface of Staphylococcus aureus, Microbes and Infection 6, pp. 604-608 (2004).

Esber HJ, et al. Specific and nonspecific immune resistance enhancing activity of Staphage Lysate, J Immunopharmacology 3, pp. 79-92 (1981).

Esber HJ, et al. Staphage Lysate: an immunomodulator of the primary immune response in mice, Immunopharmacology 10(2), pp. 77-82 (1985).

Ganfield DJ, et al. Stimulation of human lymphocytes with components of the Staphyloccal vaccine. Staphage Lysate, Federation Proceedings 44, p. 3598 (1985).

(Continued)

*Primary Examiner* — Jennifer Graser
(74) *Attorney, Agent, or Firm* — Ballard Spahr LLP

(57) ABSTRACT

The present invention relates to methods and compositions for treatment of microbial infections and for the enhancement of resistance to infection. The invention comprises administration of an effective amount of bacterial lysate compositions for the treatment of pathological conditions of microbial infections. The present invention can also be used to enhance the immune system to prevent infections by the administration of an effective amount of the compositions.

8 Claims, No Drawings

OTHER PUBLICATIONS

Gotz, et al. Purification and characterisation of an unusually heat-stable and acid/base-stable class I fructose-1,6-bisphosphate aldolase from Staphylococcus aureus, Eur J Biochem 108(1), pp. 295-301 (1980).

Kosorok, et al. Acceleration of lung disease in children with cystic fibrosis after Pseudomonas aeruginosa acquisition, Ped Pulmonol 32, pp. 277-287 (2001).

Puigdollers, et al. Immunoglobulin production in man stimulated by an orally adminstered bacterial lysate, Respiration 40, pp. 142-149 (1980).

Rossi, et al. Naturally occuring immune response against bacteria commonly involved in upper respiratory tract infections: Analysis of the antigen-specific salivary IgA levels, Immunol Lett 86, pp. 85-91 (2003).

Ruah, et al. Efficacy of a polyvalent bacterial lysate in children with recurrent respiratory tract infections, Advances in Therapy 18(4), pp. 151-162 (2001).

Ruedl, et al. Immune response in the lungs following oral immunization with bacterial lysates of respiratory pathogens, Clin Diag Lab Immunol 1(2), pp. 50-154 (1994).

Sekaninova G, et al. Pseudomonas aeruginosa phage lysate as an immunobiological agent, 1. Selection of Pseudomonas aeruginosa clinical strains for phage lysate preparation, Folia Microbiol 44(1), pp. 93-97 (1999).

West, et al. Respiratory infections with Pseudomonas aeruginosa in children with cystic fibrosis, JAMA 287(22), pp. 2958-2967 (2002).

Requirement for Restriction/Election mailed Mar. 23, 2004 by the USPTO for U.S. Appl. No. 10/367,213, filed Feb. 13, 2003 (1st Named Inventor—Pillich) (5 pages).

Response to Requirement for Restriction/Election filed May 21, 2004 with the USPTO for U.S. Appl. No. 10/367,213, filed Feb. 13, 2003 (1st Named Inventor—Pillich) (3 pages).

Non-final Rejection mailed Jul. 22, 2004 by the USPTO for U.S. Appl. No. 10/367,213, filed Feb. 13, 2003 (1st Named Inventor—Pillich) (18 pages).

Response to Non-final Rejection filed Jan. 24, 2005 with the USPTO for U.S. Appl. No. 10/367,213, filed Feb. 13, 2003 (1st Named Inventor—Pillich) (14 pages).

Notice of Allowance mailed Apr. 1, 2005 by the USPTO for U.S. Appl. No. 10/367,213, filed Feb. 13, 2003 (1st Named Inventor—Pillich) (6 pages).

Preliminary Amendment filed Jun. 30, 2005 with the USPTO for U.S. Appl. No. 11/170,972, filed Jun. 30, 2005 (1st Named Inventor—Pillich) (7 pages).

Non-final Rejection mailed Apr. 6, 2006 by the USPTO for U.S. Appl. No. 11/170,972, filed Jun. 30, 2005 (1st Named Inventor—Pillich) (8 pages).

Response to Non-final Rejection filed Jul. 10, 2006 with the USPTO for U.S. Appl. No. 11/170,972, filed Jun. 30, 2005 (1st Named Inventor—Pillich) (11 pages).

Final Rejection mailed Oct. 3, 2006 by the USPTO for U.S. Appl. No. 11/170,972, filed Jun. 30, 2005 (1st Named Inventor—Pillich) (8 pages).

Amendment after Final Rejection filed Dec. 4, 2006 with the USPTO for U.S. Appl. No. 11/170,972, filed Jun. 30, 2005 (1st Named Inventor—Pillich) (15 pages).

Amendment with Request for Continued Examination filed Mar. 2, 2007 with the USPTO for U.S. Appl. No. 11/170,972, filed Jun. 30, 2005 (1st Named Inventor—Pillich) (12 pages).

Non-final Rejection mailed Jun. 4, 2007 by the USPTO for U.S. Appl. No. 11/170,972, filed Jun. 30, 2005 (1st Named Inventor—Pillich) (6 pages).

Response to Non-final Rejection filed Aug. 28, 2007 with the USPTO for U.S. Appl. No. 11/170,972, filed Jun. 30, 2005 (1st Named Inventor—Pillich) (16 pages).

Notice of Allowance mailed Oct. 30, 2007 by the USPTO for U.S. Appl. No. 11/170,972, filed Jun. 30, 2005 (1st Named Inventor—Pillich) (4 pages).

Issue Notification mailed Jan. 23, 2008 by the USPTO for U.S. Appl. No. 11/170,972, filed Jun. 30, 2005 (1st Named Inventor—Pillich) (1 page).

Preliminary Amendment filed May 7, 2008 with the USPTO for U.S. Appl. No. 12/069,569, filed Feb. 11, 2008 (1st Named Inventor—Pillich) (6 pages).

Non-final Rejection mailed Nov. 24, 2008 by the USPTO for U.S. Appl. No. 12/069,569, filed Feb. 11, 2008 (1st Named Inventor—Pillich) (8 pages).

Response to Non-final Rejection filed Apr. 24, 2009 with the USPTO for U.S. Appl. No. 12/069,569, filed Feb. 11, 2008 (1st Named Inventor—Pillich) (7 pages).

Notice of Allowance mailed Jun. 8, 2009 by the USPTO for U.S. Appl. No. 12/069,569, filed Feb. 11, 2008 (1st Named Inventor—Pillich) (4 pages).

Issue Notification mailed Dec. 30, 2009 by the USPTO for U.S. Appl. No. 12/069,569, filed Feb. 11, 2008 (1st Named Inventor—Pillich) (1 page).

International Search Report issued Jul. 23, 2003 by the International Searching Authority for application No. PCT/US2003/004636 filed Feb. 13, 2003 (Applicant—Immunology Labs//1st Named Inventor—Pillich) (3 pages).

International Preliminary Examination Report issued Apr. 26, 2004 by the International Bureau for application No. PCT/US2003/004636 filed Feb. 13, 2003 (Applicant—Immunology Labs//1st Named Inventor—Pillich) (3 pages).

Decision to Grant issued Dec. 30, 2008 by the European Patent Office for application 03711070 filed Feb. 13, 2003 (Applicant—Immunology Labs//1st Named Inventor—Pillich) (2 pages).

Oral Proceeding Minutes issued Jul. 4, 2008 by the European Patent Office for application 03711070 filed Feb. 13, 2003 (Applicant—Immunology Labs//1st Named Inventor—Pillich) (33 pages).

Result of Consultation issued Jul. 3, 2008 by the European Patent Office for application 03711070 filed Feb. 13, 2003 (Applicant—Immunology Labs//1st Named Inventor—Pillich) (3 pages).

Written Submission Prior to Oral Proceedings filed Jun. 23, 2008 with the European Patent Office for application 03711070 filed Feb. 13, 2003 (Applicant—Immunology Labs//1st Named Inventor—Pillich) (5 pages).

Written Submission Prior to Oral Proceedings filed Jun. 20, 2008 with the European Patent Office for application 03711070 filed Feb. 13, 2003 (Applicant—Immunology Labs//1st Named Inventor—Pillich) (28 pages).

Replacement Exhibits filed May 29, 2008 with the European Patent Office for application 03711070 filed Feb. 13, 2003 (Applicant—Immunology Labs//1st Named Inventor—Pillich) (29 pages).

Written Submission Prior to Oral Proceedings filed May 27, 2008 with the European Patent Office for application 03711070 filed Feb. 13, 2003 (Applicant—Immunology Labs//1st Named Inventor—Pillich) (7 pages).

Summons to Attend Oral Proceedings issued Nov. 19, 2007 by the European Patent Office for application 03711070 filed Feb. 13, 2003 (Applicant—Immunology Labs//1st Named Inventor—Pillich) (5 pages).

Response to Examination Report filed Oct. 1, 2007 with the European Patent Office for application 03711070 filed Feb. 13, 2003 (Applicant—Immunology Labs//1st Named Inventor—Pillich) (6 pages).

Examination Report issued Mar. 28, 2007 by the European Patent Office for application 03711070 filed Feb. 13, 2003 (Applicant—Immunology Labs//1st Named Inventor—Pillich) (7 pages).

Supplemental European Search Report issued May 22, 2006 by the European Patent Office for application 03711070 filed Feb. 13, 2003 (Applicant—Immunology Labs//1st Named Inventor—Pillich) (2 pages).

Decision to Grant issued Apr. 2, 2009 by the Japanese Patent Office for application No. 2003-567189 filed Feb. 13, 2003 (Applicant—Immunology Labs//1st Named Inventor—Pillich) (1 page).

Response to Office Action filed Mar. 9, 2009 with the Japanese Patent Office for application No. 2003-567189 filed Feb. 13, 2003 (Applicant—Immunology Labs//1st Named Inventor—Pillich) (9 pages).

English Instructions for Response to Office Action issued Feb. 27, 2009 by the Japanese Patent Office for application No. 2003-567189 filed Feb. 13, 2003 (Applicant—Immunology Labs//1st Named Inventor—Pillich) (4 pages).

Office Action issued Oct. 17, 2008 by the Japanese Patent Office for application No. 2003-567189 filed Feb. 13, 2003 (Applicant—Immunology Labs//1st Named Inventor—Pillich) (6 pages) (includes English translation).
Preliminary Amendment filed Mar. 4, 2010 with the USPTO for U.S. Appl. No. 12/640,157, filed Dec. 17, 2009 (1st Named Inventor—Pillich) (4 pages).
Restriction Requirement mailed Apr. 9, 2010 by the USPTO for U.S. Appl. No. 12/640,157, filed Dec. 17, 2009 (1st Named Inventor—Pillich) (5 pages).
Response to Restriction Requirement filed Jul. 1, 2010 with the USPTO for U.S. Appl. No. 12/640,157, filed Feb. 17, 2009 (1st Named Inventor—Pillich) (6 pages).
Non-final Rejection mailed Jul. 28, 2010 by the USPTO for U.S. Appl. No. 12/640,157, filed Dec. 17, 2009 (1st Named Inventor—Pillich) (22 pages).
Response to Non-final Rejection filed Oct. 28, 2010 with the USPTO for U.S. Appl. No. 12/640,157, filed Dec. 17, 2009 (1st Named Inventor—Pillich) (14 pages).
Final Rejection mailed Dec. 27, 2010 by the USPTO for U.S. Appl. No. 12/640,157, filed Dec. 17, 2009 (1st Named Inventor—Pillich) (13 pages).
Amendment after Final Rejection filed Mar. 28, 2011 with the USPTO for U.S. Appl. No. 12/640,157, filed Dec. 17, 2009 (1st Named Inventor—Pillich) (5 pages).
Notice of Allowance mailed Apr. 28, 2011 by the USPTO for U.S. Appl. No. 12/640,157, filed Dec. 17, 2009 (1st Named Inventor—Pillich) (3 pages).
Examiner Interview mailed Apr. 28, 2011 by the USPTO for U.S. Appl. No. 12/640,157, filed Dec. 17, 2009 (1st Named Inventor—Pillich) (6 pages).
Issue Notification mailed Aug. 10, 2011 by the USPTO for U.S. Appl. No. 12/640,157, filed Dec. 17, 2009 (1st Named Inventor—Pillich) (1 page).
Requirement for Restriction/Ellection mailed Feb. 1, 2010 by the USPTO for U.S. Appl. No. 11/986,715, filed Nov. 26, 2007 (1st Named Inventor—Pillich) (5 pages).
Response to Restriction Requirement filed Jul. 1, 2010 with the USPTO for U.S. Appl. No. 11/986,715, filed Nov. 26, 2007 (1st Named Inventor—Pillich) (4 pages).
Non-final Rejection mailed Jul. 19, 2010 by the USPTO for U.S. Appl. No. 11/986,715, filed Nov. 26, 2007 (1st Named Inventor—Pillich) (19 pages).
Response to Non-final Rejection filed Oct. 19, 2010 with the USPTO for U.S. Appl. No. 11/986,715, filed Nov. 26, 2007 (1st Named Inventor—Pillich) (13 pages).
Final Rejection mailed Dec. 27, 2010 by the USPTO for U.S. Appl. No. 11/986,715, filed Nov. 26, 2007 (1st Named Inventor—Pillich) (21 pages).
Amendment after Final Rejection filed Mar. 28, 2011 with the USPTO for U.S. Appl. No. 11/986,715, filed Nov. 26, 2007 (1st Named Inventor—Pillich) (12 pages).
Notice of Allowance mailed Jul. 1, 2011 by the USPTO for U.S. Appl. No. 11/986,715, filed Nov. 26, 2007 (1st Named Inventor—Pillich) (7 pages).
Examiner Interview Summary mailed Jul. 1, 2011 by the USPTO for U.S. Appl. No. 11/986,715, filed Nov. 26, 2007 (1st Named Inventor—Pillich) (2 pages).
Examiner Interview Summary mailed Aug. 10, 2011 by the USPTO for U.S. Appl. No. 11/986,715, filed Nov. 26, 2007 (1st Named Inventor—Pillich) (2 pages).
Notice of Allowance mailed Aug. 10, 2011 by the USPTO for U.S. Appl. No. 11/986,715, filed Nov. 26, 2011 (1st Named Inventor—Pillich) (2 pages).
Issue Notification mailed Oct. 5, 2011 by the USPTO for U.S. Appl. No. 11/986,715, filed Nov. 26, 2011 (1st Named Inventor—Pillich) (1 page).
Preliminary Amendment filed Jan. 9, 2012 with the USPTO for U.S. Appl. No. 13/280,049, filed Oct. 24, 2011 (1st Named Inventor—Pillich) (6 pages).
Restriction Requirement mailed Feb. 16, 2012 by the USPTO for U.S. Appl. No. 13/280,049, filed Oct. 24, 2011 (1st Named Inventor—Pillich) (5 pages).
Response to Restriction Requirement filed Apr. 16, 2012 with the USPTO for U.S. Appl. No. 13/280,049, filed Oct. 24, 2011 (1st Named Inventor—Pillich) (3 pages).
Non-final Rejection mailed Jun. 14, 2012 by the USPTO for U.S. Appl. No. 13/280,049, filed Oct. 24, 2011 (1st Named Inventor—Pillich) (20 pages).
Response to Non-final Rejection filed Oct. 15, 2012 with the USPTO for U.S. Appl. No. 13/280,049, filed Oct. 24, 2011 (1st Named Inventor—Pillich) (10 pages).
Notice of Allowance mailed Dec. 26, 2012 by the USPTO for for U.S. Appl. No. 13/280,049, filed Oct. 24, 2011 (1st Named Inventor—Pillich) (7 pages).
Decision to Grant mailed Apr. 20, 2010 by the Korean Patent Office for application No. 2004-7012621 (1st Named Inventor—Pillich) (3 pages).
Response to Office Action filed Mar. 12, 2010 with the Korean Patent Office for application No. 2004-7012621 (1st Named Inventor —Pillich) (67 pages).
Office Action mailed Oct. 12, 2009 by the Korean Patent Office for application No. 2004-7012621 (1st Named Inventor—Pillich) (7 pages).
Supplemental Amendment and Response to Examiner's Action filed Sep. 14, 2010 with the Canadian Intellectual Property Office for application No. 2476405 (1st Named Inventor—Pillich) (5 pages).
Amendment and Response to Examiner's Action filed Sep. 10, 2010 with the Canadian Intellectual Property Office for application No. 2476405 (1st Named Inventor—Pillich) (8 pages)..
Examiner's Action mailed Mar. 11, 2010 by the Canadian Intellectual Property Office for application No. 2476405 (1st Named Inventor—Pillich) (2 pages).
U.S. Appl. No. 60/356,483, filed Feb. 13, 2003, Pillich (Immunology Labs).
U.S. Appl. No. 10/367,213, filed Feb. 13, 2003, Pillich (Immunology Labs).
U.S. Appl. No. 11/170,972, filed Jun. 30, 2005, Pillich (Immunology Labs).
U.S. Appl. No. 12/069,569, filed Feb. 11, 2008, Pillich (Immunology Labs).
U.S. Appl. No. 12/640,157, filed Dec. 17, 2009, Pillich (Immunology Labs).
U.S. Appl. No. 60/860,912, filed Nov. 24, 2006, Pillich (Immunology Labs).
U.S. Appl. No. 11/986,715, filed Nov. 26, 2007, Pillich (Immunology Labs).
U.S. Appl. No. 13/280,049, filed Oct. 24, 2011, Pillich (Immunology Labs).

* cited by examiner

COMPOSITIONS AND METHODS FOR TREATING OF MICROBIAL INFECTIONS

RELATED APPLICATION

The present application is a continuation of, and claims priority to U.S. application Ser. No. 12/640,157, filed Dec. 17, 2009, now U.S. Pat. No. 8,007,817, which is a continuation of U.S. application Ser. No. 12/069,569, filed Feb. 11, 2008, now U.S. Pat. No. 7,648,707, which is a continuation of U.S. application Ser. No. 11/170,972, now U.S. Pat. No. 7,329,409, filed Jun. 30, 2005, which is a continuation of U.S. application Ser. No. 10/367,213, now U.S. Pat. No. 6,929,798, filed Feb. 13, 2003, which claims benefit of U.S. Provisional Application Ser. No. 60/356,483, filed Feb. 13, 2002, each of which is incorporated herein in its entirety.

FIELD OF THE INVENTION

The present invention relates generally to the treatment of microbial infections. More specifically, the invention relates to methods and compositions for the enhancement of an immune response in a human or animal to microbial infections.

BACKGROUND OF THE INVENTION

The idea of using phages for treatment of infectious diseases was initially proposed by d'Herelle in 1917. In the 1920s, the discovery of bacteriophages was thought to be the answer for treatment of bacterial infections. Bacteriophages invade and destroy bacteria and appeared to be the selective therapeutic bullet that would knock out bacteria invading an animal or plant host. Unfortunately, the phages were not as effective in killing bacteria in host organisms as they were in killing bacteria in vitro. The development of antibiotics in the 1940s as the preferred treatment for bacterial infections led to a decline in research into use of bacteriophages for treatments of infectious diseases.

In a few countries, notably in Eastern Europe and India, research continued in the use of bacteriophages and bacterial lysates for treatment of infectious diseases and enhancement of immune responses. Though much of that research is still not accepted widely in other industrialized countries, a renewed interest in this research is growing as a result of the occurrence of antibiotic resistant bacteria. Many infectious diseases that were once easily treatable with antibiotics are now a serious health threat because the bacteria are resistant to most, if not all, antibiotics. Medical science is searching for treatments that can respond to these resistant bacteria in a way that does not lead to even more resistant infectious strains.

The U.S. Centers for Disease Control and Prevention estimates that 20% to 50% of prescribed antibiotics are unnecessary. The overuse of antibiotics in medicine and agriculture has greatly fostered the development of resistant strains of bacteria. In a microenvironment bombarded with antibiotics, the few bacteria that can resist the drugs proliferate. Bacteria are becoming increasingly resistant to what were previously considered "last resort" antibiotics.

Bacteriophage therapy has not gained much attention or acceptance in most industrialized countries, in part due to the reliance on pharmaceuticals, such as antibiotic treatment for bacterial infections. With the advent of increased bacterial resistance, bacteriophage therapy has come under renewed scrutiny as a possible alternative to pharmaceutical treatments of bacterial infections. What is needed are compositions and methods for treatment and prevention of microbial infections that do not rely on pharmaceutical antibiotic therapies. Such methods and compositions should be capable of treating or preventing infections in organisms, including humans, animals and plants.

SUMMARY OF THE INVENTION

The present invention is directed towards compositions and methods of treatment and prevention of microbial infections. Preferred methods include administration of compositions comprising bacterial lysates. The present invention contemplates use of any bacterium that has stable reproduction and does not produce a toxin or have deleterious effects either on the bacteriophage or on the human or animal receiving the resulting lysate. Preferred bacterial lysates include, but are not limited to, those derived from strains of *Staphylococcus aureus* (*S. aureus*), *Klebsiella pneumoniae*, (*K. pneumoniae*) and *Pseudomonas aeruginosa* (*P. aeruginosa*). Most preferred bacterial strains comprise bacterial strains deposited at the Czech Collection of Microorganisms (CCM) having accession numbers, CCM 4992, CCM 4993, CCM 4994, CCM 4995, CCM 4996, CCM 4997, CCM 4998. Most preferred bacteriophages comprise bacteriophages deposited at the Deutsche Sammlung von Mikroorganismen und Zellkulturen GmbH (DSM) and having accession numbers, 14614, 14615, and 14616.

The present invention comprises a composition, comprising a bacterial lysate derived from the infection of at least one bacterial strain of *S. aureus*, *K. pneumoniae*, or *P. aeruginosa* with a bacteriophage. The composition of the present invention further comprises a bacterial lysate derived from one or more *S. aureus* bacterial strains deposited with the CCM under accession numbers CCM 4992, CCM 4993, CCM 4994, CCM 4995, CCM 4996, CCM 499$^1$7, and CCM 4998. The present invention also comprises a bacterial lysate derived from bacteriophages deposited with the DSM having accession numbers DSM 14614, DSM 14615, and DSM 14616. The present invention additionally comprises *S. aureus* bacterial isolates deposited with the CCM under accession numbers CCM 4992, CCM 4993, CCM 4994, CCM 4995, CCM 4996, CCM 4997, and CCM 4998. The present invention also comprises bacteriophages, deposited with the DSM under accession number DSM 14614, DSM 14615, and DSM 14616.

The bacterial lysates of the present invention may be used in methods of treating or preventing pathological conditions of microbial infections in humans or animals. The compositions and inventions of the present invention may further comprise a suitable pharmaceutical excipient. The pathological conditions of microbial infections which can be treated or prevented by the present invention include, but are not limited to, conditions such as chronic upper respiratory disease, wound infection, osteomyelitis, endocarditis, skin polymicrobial infections, bronchial asthma, chronic sinusitis, cystic fibrosis or acne vulgaris.

The compositions of the present invention may be used as vaccine compositions as well as in the treatment specific microbial infections. The compositions of the present invention may consist of one or more bacterial lysates formed by infecting specific strains of bacteria with bacteriophages. The compositions can be used in methods for the treatment and prevention of local or systemic bacterial infections including, but not limited to, chronic or recurrent respiratory or ear infections, post operational infections, bacterial pneumonia infections, sepsis, skin infections, wound infection, osteomyelitis, allergies, asthma, sinusitis, and acne vulgaris. Additionally, the compositions of the present invention may be used in methods for immune stimulation.

DETAILED DESCRIPTION OF THE INVENTION

The present invention comprises compositions and methods for the treatment of microbial infections comprising administering an effective amount of one or more bacterial lysates or mixtures thereof. The immunogenic compositions of the present invention may further comprise at least one or more immunogenic or immunostimulating materials or formulations for regulating or affecting microbial distribution in an organism.

The present invention also comprises compositions and methods of vaccination against microbial infections comprising administering compositions comprising one or more bacterial lysates or mixtures thereof and a pharmaceutically acceptable carrier. The lysates may be used individually or in combination. The vaccines of the present invention are used to immunize animals, including humans, against bacterial diseases by administering to the human or animal an effective immunizing amount of the bacterial lysate.

The compositions of the present invention comprise bacterial lysates produced by infecting selected bacteria with selected bacteriophages. The present invention contemplates use of any bacteriophage that stably reproduces in a selected bacterial strain and does not result in the production of a significant amount of a toxin or another component that has deleterious effects either on the host bacteria or in the resulting lysate that is deleterious to the human or animal receiving the lysate. Determination and selection of such bacteriophages are performed using techniques known to microbiologists and include testing for long term stability in a general host strain, long term persistence of virulence, stability and reproducibility of lysis and reproducibility of resultant lysates. The host strain is a strain which is extremely sensitive to the lytic properties of the bacteriophage. It is selected from the strains sensitive to the particular bacteriophage.

The compositions of the present invention further comprise bacterial lysates derived from selected bacteria. The present invention contemplates use of any bacterium that has stable reproduction and does not produce a toxin that has deleterious effects either on the bacteriophage or in the lysate recipient. Determination and selection of such bacteria is performed using techniques known to those skilled in the art and includes testing for the absence of toxins particularly: alpha toxin, beta toxin, delta toxin, gamma toxin, enterotoxins A, B, C, and D, Toxic Shock Syndrome Toxin (TSST), exfoliatins A and B, leukocidin, fatty acid modifying enzyme, and hemolysins. Testing also includes tests for stability and reproducibility of lysates generated by the phage-induced lysis, long-term sensitivity of the bacterial strains, and continued susceptibility of the bacteria to lysis by phages without the appearance of phage-resistant colonies.

Selection of a lysate composition is determined by the methods of use for a particular lysate composition. For example, if the desired use is to provide immunity for staphylococcal infections, one or more strains of staphylococcal bacteria are used as the bacterial host organisms. In this same example, one or more bacteriophages that are specific for staphylococcal bacteria, or are at least capable of having a productive infection in staphylococcal bacteria, are used to create the staphylococcal lysate. Alternatively, one bacterial strain may be grown to produce a bacterial culture or bacterial broth and then separate aliquots of the bacterial culture are each infected with a different bacteriophage to create individual lysates. These individual lysates may be used individually or combined to form compositions. In another embodiment, different bacterial strains are grown and then each is infected with the same bacteriophage to yield lysate compositions that can be used individually or combined to form compositions. Another embodiment of the present invention contemplates the use of different bacterial strains that are each infected with different bacteriophages and the resulting lysates are used individually or in combination to form compositions.

The compositions of the present invention preferably comprise compositions comprising lysates from at least one bacterial strain, more preferably, two or more bacterial strains. A preferred composition comprises lysates from one of the following bacteria: Staphylococcus aureus (S. aureus), Klebsiella pneumoniae (K. pneumoniae), and Pseudomonas aeruginosa (P. aeruginosa). Preferred compositions comprise lysates derived from bacterial strains of S. aureus deposited with the Czech Collection of Microorganisms (CCM) on Oct. 11, 2001 and having accession nos. CCM 4992, CCM 4993, CCM 4994, CCM 4995, CCM 4996, CCM 4997 and CCM 4998. Preferred compositions additionally comprise the bacterial strains deposited with the CCM on Oct. 11, 2001 and having accession numbers CCM 4992, CCM 4993, CCM 4994, CCM 4995, CCM 4996, CCM 4997 and CCM 4998

The methods of the present invention comprise the use of bacteriophages to yield the desired bacteriophage lysates. A more preferred method comprises lysates produced by bacteriophages for S. aureus, K. pneumoniae, and P. aeruginosa. Most preferred methods comprise lysates derived from bacteriophages deposited on Nov. 19, 2001 with the Deutsche Sammlung von Mikroorganismen und Zellkulturen GmbH (DSM) and having accession numbers 14614, 14615, and 14616. Preferred compositions additionally comprise the bacteriophages deposited on Nov. 19, 2001 with the Deutsche Sammlung von Mikroorganismen und Zellkulturen GmbH (DSM) and having accession numbers 14614, 14615, and 14616. The bacteriophages can be used alone or in combination to lyse one or more different bacterial strains.

Generally, the methods of the present invention comprise growing one or more desired bacterial strains to a desired concentration. For example, ranges of preferred concentrations of bacterial cultures are from $1 \times 10^6$ to $1 \times 10^{12}$ cells/ml, preferably $1 \times 10^7$ cells/ml, $1 \times 10^8$ cells/ml, $1 \times 10^9$ cells/ml, $1 \times 10^{10}$ cells/ml, $1 \times 10^{11}$ cells/ml. At the selected time, one or more bacteriophages, at an effective concentration, are added to the bacterial culture. For example, ranges of preferred concentrations of bacterial phage cultures are from $1 \times 10^8$ to $1 \times 10^{12}$, preferably, $1 \times 10^9$, $1 \times 10^{10}$, $1 \times 10^{11}$. Infection and lysis by the bacteriophages is allowed to proceed. Incubation of the bacteriophage or phages with the bacterial culture can be from 3 to 48 hours. The resulting bacterial lysate is then filter sterilized using filters having a pore size from <0.1 μm to 0.45 μm.

Both the material retained on the filter, the rententate, and the flow through material, the filtrate, are kept. It is preferred to use the filtrate for compositions in methods of treatment and immune stimulation. In general, the filtrate comprises cellular materials such as components of cell walls, cellular membranes, proteins, ribosomal fractions, glycoproteins, DNA, RNA, and the like. The rententate from ultrafiltration using filters with a pore size of <0.1 micrometers comprises larger cellular materials and unlysed cells and bacteriophages which may also be used in the compositions and methods of the present invention.

The use of bacteriophages to prepare lysates is effective for all types of bacteria and allows the preparation of lysates to evolve with the bacteria and avoid resistance problems common to pharmaceuticals. The use of bacteriophage lysates allows the preparation of products capable of modulating the immune system prepared from a single bacterial strain, or a combination of bacterial strains.

In general, methods of the present invention comprise screening strains of a particular bacterial family or group that does not produce toxins, for selected bacteria that exhibit the most common antigenic pattern found in the bacterial family or group. The antigenic pattern can be determined by immunogenic methods such as fluorescent antibody identification, FACS selection, ELISA, Western blots, SDS gel electrophoresis or by other detection methods known to those skilled in the art. Cultures of the selected bacteria are then infected by the introduction of phage homologues. The combination is screened for strains that result in quantitative lysis of bacteria in a given time and strains that exhibit the most common antigenic pattern. The bacterial strain and phage are then preserved, preferably by lyophylization, to maintain stability. The stability of the bacterial strains and phages are determined through stability assays, repeated cultures and subcultures on media. The bacterial strains and phages are also checked for antigenic infection and reproducibility of antigenic patterns of lysates. At least one, preferably two or more, of the resultant lysates are combined to yield an immunomodulator composition. Therefore, the resulting lysate from the lysis can be quantitatively and qualitatively analyzed by SDS gel electrophoresis.

The compositions can be used in methods for the treatment of local or systemic bacterial infections including, but not limited to, chronic or recurrent respiratory or ear infections, prophylactic prevention of infections and treatment of pathological conditions of microbial infections such as post operational infections, bacterial pneumonia infections, sepsis, skin infections, wound infection, osteomyelitis, skin polymicrobial infections, allergies, asthma, endocarditis, arthritis, abscess, sinusitis, and acne vulgaris. Additionally, bacteriophage lysates can be used in methods for immune stimulation such as vaccines that boost the immune system. The compositions can also be administered for several months prior to planned operations such as knee or hip replacements to boost general immune response, decrease recovery time, and prevent nosocomial infections.

Methods of treatment contemplated by the present invention comprise administration of an effective amount of a bacterial lysate composition to an organism having an infection or in need of immune stimulation. An effective amount of a bacterial lysate composition can be determined by using known amounts of such compositions, or by starting treatment with a small dose and increasing the dose until the desired effect is achieved. Such techniques for determining effective amounts are known to those skilled in the art and do not require undue experimentation to determine. Differing routes of administration including, but not limited to, oral, buccal, nasal, aerosol, topical, transdermal, injectable, slow release, controlled release, iontophoresis, sonophoresis, intravenous, intramuscular, intraperitoneal, intraspinal, intrathecal, intracerebroventricular, intraarterial, subcutaneous and intranasal routes, generally require differing effective amounts to achieve the desired result. For example, oral administration may require different effective amounts than topically administered effective amounts. In general, a range of 0.0001 mg/kg/day to 500 mg/kg/day provides an effective amount of a bacterial lysate composition.

Preferred methods comprise administration of the lysate three to six weeks prior to reconstructive surgery such as, but not limited to, a knee or hip replacement. For example, the lysate is administered in a dose is 0.05 cc, injected intradermally twice a week. Three days after administration of the initial dose, the patient is observed for tolerance of the lysate. If no local reaction is noted, the dose can be increased to 0.1 cc up to 0.2 cc. The lysate is then administered every other day. In the case of nasal routes of administration, preferably two to four drops are placed in each nostril the first four days and after four days, the dosage is repeated every other day. The length of treatment is generally three to four months. Multiple methods of administration may be combined with the length of treatment depending on the immune status of the patient.

The present invention further comprises methods of eliciting an immune response in a host comprising administering an effective amount of an immunogenic composition. The immunogenic composition may be used prophylactically as part of a vaccination system in which the composition is administered prior to infection, or in the treatment of a particular infection. The immune response may be a humoral or a cell-mediated immune response. Immunogenicity may be improved the co-administration of antigens with adjuvants. Adjuvants may act by retaining the antigen locally near the site of administration facilitating a slow sustained release of antigen to cells. Adjuvants can also attract immune cells to the site of injection and stimulate such cells to elicit immune responses. A wide range of adjuvants can aid in evoking an immune responses. These include, but are not limited to, pluronic polymers with mineral oil, Freund's complete adjuvant, lipid A, liposomes and cholera toxin subunit B or its genetically modified variants.

The following specific examples of the methods and compositions of the present invention are in no way to be seen as limiting, but merely provide illustrative embodiments for the applications of the present invention. The present invention contemplates the use of bacterial lysates for the treatment of bacterial and other microbial infections and for stimulation of the immune system in general and other disease treatments or compositions are not limited by the specific examples taught herein.

*Staphylococcus aureus* Infections Prevention and Treatment

Staphylococcal bacteria, and *S. aureus* in particular, are some of the more common and virulent pathogens. Some staphylococcal infections are characterized by intense suppuration, necrosis of local tissues and the formation of abscesses. Staphylococcal infections are responsible for skin infections, such as furuncles, carbuncles and impetigo, and deep lesions spreading from the skin into bones, joints, soft tissues and organs. *S. aureus* can produce toxins leading to scalded skin syndrome, toxic shock syndrome and staphylococcal food poisoning. It is a major cause of wound infection and a continuing cause of hospital epidemics. *S. aureus* is currently resistant to many classes of antibiotics and is currently being treated with vancomycin as a last resort. However, strains resistant to vancomycin have already begun to appear.

*S. aureus* has many virulence factors that act against native or adaptive immune responses. While not wishing to be bound by any particular theory, it is currently believed that part of the innate response against *S. aureus* comprises the Toll-like receptor (TLR) family. TLRs are transmembrane receptors linking the pattern recognition system of pathogens with intracellular signaling. In humans, the TLR family is represented by TLR (TLR 1-10), several proteins related to TLR (RP105, Nod1, Nod2), as well as lipopolysaccharide (LPS) receptor (CD14). Several TLRs appear to have a specific function in the pattern recognition system. For example, TLR-2 is believed to activate cells in response to gram-positive cell-wall components (peptidoglycan). TLR-4 is important (in complex with CD14) for recognition of LPS (gram-negative bacteria). TLR-9 recognizes CpG motif of bacterial DNA. The activation of the innate immune system induces early inflammatory reaction mediated by monocytes, neutrophils, and endothelial cells. The response can occur with or without participation of the adaptive immune system, leading to leukocyte recruitment, production of pro-inflammatory cytokines (TNF-alpha, IL-1 beta), reactive oxygen products, and effector cytokines (e.g., IL-12) acting on T cells, antigen presenting cells, and by a cascade of cytokines indirectly on B cells.

Mice deficient in TLR-2 or a signaling molecule (MyD88) were highly susceptible to *S. aureus* infection (J. Immunol. 165, 5392-5396, 2000). Furthermore, wild-type mice became more resistant to acute polymicrobial sepsis after treatment with CpG DNA (J. Immunol. 165, 4537-4543, 2000) that is currently believed to act via TLR-9. TLR-2 is likely to play an important role in human *S. aureus* infection as evidenced by detection of TLR-2 polymorphism associated with *S. aureus* septic shock (Infect. Immun. 68, 6398, 2000). Activation of TLR-2 receptor with *S. aureus* cell wall components results in upregulation of Th-1 pathway (TNF-alpha, interpheron gamma, IL-1, etc.). Increase of these pro-inflammatory cytokines activates and modulates multiple responses of innate and adaptive immunity.

*S. aureus* has several mechanisms to interfere with the normal immune response. Not only has the bacteria developed a resistance against antimicrobial proteins but it can also survive inside neutrophils. In addition, various strains of *S. aureus* possess some of the battery of toxins and enzymes and other products that enhance infectivity and bacterial survival and proliferation. Antibodies specific against toxins and enzymes and other soluble products neutralize the activities of the toxins while antibodies specific against cells and cellular components opsonize the targeted cells and enhance their phagocytosis.

Treatment of staphylococcal infections and *S. aureus* in particular, are provided by the present invention. Selected staphylococcal lysate compositions comprising lysate from single or multiple strains of *staphylococcus* and bacteriophages are administered through various routes, including but not limited to, nasal drops and subcutaneous routes, or a combination thereof. Lysates from different strains of *staphylococcus or* lysates that result from different bacterial phage inoculations are preferably combined in equal proportions. Staphyloccocal lysate (SPL) has been clinically effective in the treatment of all staphylococcal infections of adults, as well as chronic conditions in pediatrics (chronic upper respiratory diseases, bronchial asthma, chronic sinusitis, cystic fibrosis) and in dermatology (acne vulgaris).

SPL is prepared by lysis of *S. aureus* culture with a polyvalent bacteriophage. Most staphylococcal phages belong to the Siphoviridae family, e.g., phages with double-stranded linear DNA and with long, noncontractile tails. SPL is a complex of antigenic components of ribosomal, cytoplasmic, nuclear, cell wall, and membranous origin. Purified components of SPL can be used for specific stimulation of certain pathways including, but not limited to, peptidoglycans via TLR-2, CpG DNA via TLR-9.

Alternatively, animals and humans can be vaccinated with SPL compositions so that staphylococcal infections are resisted. Such treatment comprises administration of a SPL composition comprising lysed bacteria and phage through routes of administration comprising subcutaneous injections, nasal drop application and lavage of osteomyelitis fistulas. The administration of the lysate compositions can take place prophylacticly, prior to the occurrence of a staphylococcal infection, as well as during a staphylococcal infection. Preferred times of prophylactic administration are after the age of three for three to six weeks prior to potential infections situations or generally as part of a vaccination program.

*Klebsiella pneumoniae* Infection Prevention and Treatment

Another bacteria group for which the present invention is effective is the *Klebsiella* bacteria, in particular, *K. pneumoniae*. *K. pneumoniae* is a nonopportunistic pathogen normally found in the gut. Outside of the gut, it is a growing source of hospital-acquired infections causing pneumonia and urinary tract infections. Patients with chronic respiratory diseases, diabetics, alcoholics, and people of advanced age, as well as those using respiratory therapy devices, intravenous and urinary catheters are particularly sensitive to acquiring infectious *Klebsiella*.

Classically, *K. pneumoniae* infection of the respiratory tract causes a severe, rapid-onset illness that often results in destruction of areas in the lung. Even with treatment, the mortality rate due to *K. pneumoniae* is 50%. Infected persons generally develop high fever, chills, flu-like symptoms and a cough that produces a lot of mucous. While normal bacterial pneumonia frequently resolves without complication, *K. pneumoniae* frequently causes lung destruction and abscesses.

*Klebsiella* can also cause less serious respiratory infections, such as bronchitis, which is usually a hospital-acquired infection. Other common hospital-acquired infections caused by *Klebsiella* are urinary tract infections, surgical wound infections and bacteremia. All of these infections can progress to shock and death if not treated early in an aggressive fashion.

Methods of treatment of *Klebsiella* infections and *K. pneumoniae* in particular, are provided by the present invention. Selected *klebsiella* lysate compositions comprising single or multiple strains of *klebsiella* or bacteriophages are administered through various routes, including but not limited to, nasal drops and subcutaneous routes, or a combination thereof. The lysate compositions are administered daily until the desired treatment is achieved.

Alternatively, animals and humans can be vaccinated or treated prophylactically with bacterial lysate compositions so that *klebsiella* infections are resisted. Such treatment comprises administration of *klebsiella* lysate compositions comprising lysates from single or multiple strains of *klebsiella* and phage through routes of administration comprising nasal drops and subcutaneous administration at times prior to infection with *klebsiella*. Preferred prophylactic administration for humans is after the age of 3, for 3-6 weeks prior to potential infectious conditions such as hospitalizations or generally as part of a vaccination program.

*Pseudomonas aeruginosa* Infection Prevention and Treatment

Another frequent hospital contaminant, *P. aeruginosa* is a versatile, gram-negative bacterium that grows in soil, marshes, and coastal marine habitats, as well as on plant and animal tissues. *P. aeruginosa* is able to grow in aqueous solutions including distilled water. This ability results in frequent contamination of i.v. fluids, respirators, anesthesia equipment and other hospital equipment. People with cystic fibrosis, burn victims, individuals with cancer, and patients requiring extensive stays in intensive care units are particularly at risk of *P. aeruginosa* infection. Unlike many environmental bacteria, *P. aeruginosa* has a remarkable capacity to cause disease in susceptible hosts. It has the ability to adapt to and thrive in many ecological niches, from water and soil to plant and animal tissues. *P. aeruginosa* can produce a number of toxic proteins which not only cause extensive tissue damage, but also interfere with the immune system's defense mechanisms. These proteins range from potent toxins that enter and kill host cells at or near the site of colonization to degradative enzymes that permanently disrupt the cell membranes and connective tissues in various organs.

*P. aeruginosa* infections are a particular problem in individuals with cystic fibrosis. Cystic fibrosis is a common lethal genetic disease (incidence 1:2,000 Caucasian births). The disease presents with a history of chronic lung disease, recurrent pneumonia, cough, and bronchiectasis. The lungs of cystic fibrosis patients may be colonized with *P. aeruginosa*, particularly a special mucoid strain that contributes to fatal complications. *S. aureus* is frequently present as well.

Treatment of *pseudomonas* infections and *P. aeroginosa* in particular, are provided by the present invention. Selected *pseudomonas* lysate compositions comprising lysates from single or multiple strains are administered through various routes, including but not limited to, nasal drops and subcutaneous routes, or a combination thereof.

Alternatively, animals and humans can be vaccinated with *pseudomonas* lysate compositions so that *pseudomonas* and pneumococcal infections are resisted. Such treatment comprises administration of *pseudomonas* lysate composition comprising lysates from bacteria and phage through routes of administration comprising nasal and subcutaneous injection at times prior to infection with *pseudomonas*. Preferred times of preventative administration are after 3 years of age, for three to six weeks prior to the potential infectious situations such as proposed hospitalization or generally as part of a vaccination program.

Mastitis

The present invention is effective for the prevention and treatment of mastitis, particularly mastitis in dairy cattle, though any mastitis can be treated using the present invention. Mastitis in dairy cattle is an inflammation of the mammary gland in response to intramammary bacterial infection, mechanical trauma, or chemical trauma. Economic losses due to mastitis are $1.7 billion dollars a year in the U.S. alone. It is thought that contagious mastitis is primarily caused by *S. aureus* and *Streptococcal agalactiae*. Environmental mastitis can be caused by a variety of different bacteria, including, but not limited to, *K. pneumoniae, Escherichia. coli, Klebsiella oxytoca, Enterobacter aerogenes, Streptococcal uberis, Streptococcal bovis*, and *Streptococcal dysgalactia*.

Traditional prevention of bovine mastitis involves a complex regimen of daily teat-dipping with a disinfectant solution, and may involve antibiotic-containing teat dips. When infection does occur, intramammary infusion of antibiotics is indicated, however this leads to increasingly resistant strains of bacteria. Antibiotic therapy can reduce the infection so that the milk produced is saleable, but it generally does not lead to complete elimination of the causative organism. While not wishing to be bound to any particular theory, studies on mastitis have indicated that part of the problem in treating mastitis is that a significant number of bacteria remain viable in the mammary gland within phagocytic polymorphonuclear neutrophil leukocytes (PMN). When lysis of the leukocyte occurs, the phagocytized bacteria may provide a renewed source of mastitis producing, for example, staphylococcal regrowth. While not wishing to be bound, it is currently believed that the use of bacterial lysates allows for the creation of memory cells, allowing the cow to respond to remaining bacteria, whenever they might appear.

In general, bovine mastitis is treated by administering an effective amount of a bacterial lysate to a cow. The administration may be a prophylactic administration, in that all cattle in the herd are treated with bacterial lysate compositions, or the administration may occur when infection occurs in individual cows. For example, in heifers, vaccination starts at 6 months of age. Three subcutaneous injections of lysate (5 cc each) are applied between 6 and 24 months of age.

The present invention is also useful in the treatment of skin infections in other domesticated animals including canine and feline staphylococcal skin infection, dermatitis, and other chronic infections. Treatment methods comprise the administration of an effective amount of a bacterial lysate to domesticated animals.

Bacterial antigens are known to trigger immunomodulatory effects in vivo. For example, in an infection of a host by a staphylococcal organism, other bacteria and some viruses, it is believed that a *staphylococcus* lysate composition potentiates cell-mediated as well as humoral immunity in animals and humans. Treatment with *staphylococcus* lysates elevates antigen specific as well as total humoral antibody and immunoglobulin levels creating an effective immunoadjuvant for humoral responses as well.

Delivery and Dosage

The methods of the present invention comprise routes of administration that include, but are not limited to, oral, buccal, nasal, aerosol, topical, transdermal, injectable, slow release, controlled release, iontophoresis, sonophoresis, and other delivery devices and methods. Injectable methods include, but are not limited to, intravenous, intramuscular, intraperitoneal, intraspinal, intrathecal, intracerebroventricular, intraarterial, subcutaneous and intranasal routes.

The compositions for treating the pathologies by the present invention can further include a pharmaceutically acceptable carrier or excipient. The compositions can also include other medicinal agents, pharmaceutical agents, carriers, adjuvants diluents and other pharmaceutical preparations known to those skilled in the art. These agents are known to those skilled in the art and are generally described as being biologically inactive and can be administered to patients without causing deleterious interactions with the active agent.

According to the invention, at least one pharmaceutical composition can be delivered by any of a variety of inhalation or nasal devices known in the art for administration of a therapeutic agent by inhalation. Devices capable of depositing aerosolized formulations in the sinus cavity or alveoli of a patient include metered dose inhalers, nebulizers, dry powder generators, sprayers, and the like. Other devices suitable for directing pulmonary or nasal administration are also known in the art.

There are a several desirable features of an inhalation device for administering a compound of the present invention. For example, delivery by the inhalation device is advantageously reliable, reproducible, and accurate. For pulmonary administration, at least one pharmaceutical composition is delivered in a particle size effective for reaching the lower airways of the lung or sinuses.

All such inhalation devices be used for the administration of a pharmaceutical composition in an aerosol. Such aerosols may comprise either solutions (both aqueous and non aqueous) or solid particles. Metered dose inhalers like the Ventolin® metered dose inhaler, typically use a propellant gas and require actuation during inspiration. See, e.g., WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each entirely expressly incorporated herein by reference. Nebulizers like AERx®, Aradigm, the Ultravent® nebulizer (Mallinckrodt), and the Acorn II® nebulizer (Marquest Medical Products), the above references entirely expressly incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of the invention, and are not intended as limiting the scope of the invention.

Suitable formulations, wherein the carrier is a liquid, for administration, as for example, a nasal spray or as nasal drops, include aqueous or oily solutions of the active ingredient.

A spray comprising a pharmaceutical composition of the present invention can be produced by forcing a suspension or solution of a compound disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of composition protein either directly or through a coupling fluid, creating an aerosol including the composition protein.

In a metered dose inhaler (MDI), a propellant, a compound of the present invention, and any excipients or other additives are contained in a canister as a mixture including a liquefied, compressed gas. Actuation of the metering valve releases the mixture as an aerosol.

Pharmaceutical compositions for use with a metered-dose inhaler device will generally include a finely divided powder containing a compound disclosed herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. One of ordinary skill in the art will recognize that the methods of the present invention can be achieved by pulmonary administration of a compound disclosed herein via devices not described herein.

Simple lysate delivery systems of the present invention comprise capsules containing differently coated pellets of the lysate. On release from the capsule, the uncoated pellets provide an initial amount of the lysate composition to the body, and the coated pellets provide the lysate composition over a period of time. Another system includes hydrogel materials with coated pills embedded in the hydrogel, such as that taught in U.S. Pat. No. 4,659,558. The unswollen hydrogel, such as that taught in U.S. Pat. No. 4,659,558, is swallowed and in the presence of fluids in the stomach, swells so that the hydrogel is retained within the stomach. The coated pills are released as the hydrogel degrades. The lysate may also be administered through the use of auto-injection devices such as those described in U.S. Pat. Nos. 5,514,097; 159,192; and 5,643,214; as well as European Patent No. 0 516 473 B1.

In controlled release systems contemplated in the present invention, after oral ingestion, lysates are released by diffusion and erosion throughout the gastrointestinal tract to a significant degree. Methods of the present invention for the prolongation of gastric retention time include incorporation of fatty acids to reduce physiological gastric emptying and the use of bioadhesive polymers. Such systems are known to those skilled in the art and comprise using polymers such as polycarbophyll, sodium carboxymethylcellulose, tragacanth gum, acrylates and methacrylates, modified celluloses and polysaccharide gums.

Another delivery system that is contemplated by the present invention for targeting lysates to the stomach while avoiding gastric emptying is known as a hydrodynamically balanced system. This system is based on capsules or tablets with bulk density lower than gastric fluid. Thus, the dosage form stays buoyant in the stomach. These dosage forms are comprised of 20-75% of one or more hydrocolloids, e.g., hydroxyethylcellulose and hydroxypropylmethylcellulose.

Other types of these devices include osmotic pressure compartments containing osmotically active salts. In the present invention, dissolution of these salts by the gastric fluid pumps out the lysate composition. Others are based upon a floating bilayer compressed matrix. One of the layers is comprised of a hydrophilic polymer and a carbon dioxide generating composition. The carbon dioxide maintains buoyancy and the other hydrophilic layer releases the drug from the matrix. A further method for gastric lysate targeting involves an intragastric retention shape, made of polyethylene or polyethylene blend.

The delivery systems described above may also be used in the present invention to target lysate compositions to the upper small intestine. However targeting to other areas of the small intestine may involve several additional systems. The low stomach pH and presence of gastric enzymes have led to the development of enteric coating. This coating protects the gastric mucosa from lysate irritation. Coating is done with a selectively insoluble substance, and protects lysates from inactivation by gastric enzymes and/or low pH.

In summary, the present invention comprises methods of administration of lysate compositions for treatment of microbial infections. Not all administration routes are efficacious for every patient. Therefore, the present invention comprises various methods, which require differing formulations of the lysate compositions. The formulations include those suitable for oral, rectal, ophthalmic (including intravitreal or intracameral), nasal, topical (including buccal and sublingual), vaginal or parenteral (including subcutaneous, transdermal, intramuscular, intravenous, intradermal, intratracheal, and epidural) administration. The formulations may conveniently be presented in unit dosage form and may be prepared by conventional pharmaceutical techniques.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molding, in a suitable machine, a mixture of the powdered compound moistened with an inert liquid diluent may make molded tablets. The tablets may be optionally coated or scored and may be formulated so as to provide a slow or controlled release of the lysate therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the lysate in a suitable liquid carrier.

The present invention additionally comprises methods of topical administration. To prepare the topical composition according to the present invention the usual manner for preparing skin care products may be employed. The active components are generally incorporated in a dermatological acceptable carrier in conventional manner. It may be packaged in discrete units including aerosol sprays, each containing a predetermined amount of the active ingredient, as a powder, stick, or granules, as creams, pastes, gels, lotions, syrups, or ointments, on sponges or cotton applicators, or as a solution or a suspension in an aqueous liquid, a non-aqueous liquid, an oil-in-water emulsion, or a water-in-oil liquid emulsion. The lysates can suitably first be dissolved or dispersed in a portion of the water or another solvent or liquid to be incorporated in the composition. The composition can also be in the form of a so-called "wash-off" product e.g. a bath or shower gel, possibly containing a delivery system for the lysates to promote adherence to the skin during rinsing. Most preferably the product is a "leave-on" product; a product to be applied to the skin without a deliberate rinsing step soon after its application to the skin. Such compositions may be prepared by any of the methods of pharmacy, but all methods include the step of bringing into association the carrier(s) with the lysate composition. In general, the compositions are prepared by uniformly and intimately admixing the active ingredient with liquid carriers or finely divided solid carriers or both, and then, if necessary, shaping the product into the desired presentation. The composition may packaged in any suitable manner such as in a jar, a bottle, tube, roll-ball, or the like, in the conventional manner.

Formulations suitable for vaginal administration may be presented as pessaries, tamports, creams, gels, pastes, foams or spray formulations containing in addition to the lysates such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers. Extemporaneous injection solutions and suspensions may be prepared from sterile powders, granules and tablets of the kind previously described. Preferred unit dosage formulations are those containing a daily dose or unit, daily sub-dose, as herein above recited, or an appropriate fraction thereof, of the administered ingredient.

The compounds may also be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions. REMINGTON'S PHARMACEUTICAL SCIENCES (A. Osol ed., 16th ed. (1980)).

In a specific embodiment, the compounds disclosed herein are formulated as liposomes. Liposomes containing a compound of the present invention are prepared by methods known in the art. See, e.g., U.S. Pat. Nos. 5,013,556; 4,485, 045; 4,544,545; WO 97/38731; Epstein et al., 82 PROC. NATL. ACAD. SCI. USA 3688 (1985); and Hwang et al., 77 PROC. NATL. ACAD. SCI. USA 4030 (1980). The compounds of the present invention can also be administered in the form of liposome delivery systems such as small unilamellar vesicles, large unilamellar vesicles, and multilamellar vesicles. Liposomes can be formed from a variety of phospholipids such as cholesterol, stearylamine or phophatidylcholines.

The present invention provides stable formulations as well as preserved solutions and formulations containing a preservative as well as multi-use preserved formulations suitable for pharmaceutical or veterinary use, comprising at least one compound disclosed herein in a pharmaceutically acceptable formulation. Formulations in accordance with the present invention may optionally contain at least one known preservative.

In addition, co-administration or sequential administration of the compounds of the present invention and other therapeutic agents may be desirable, such as chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

In another embodiment, the other therapeutic agent comprises a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

It should be understood that in addition to the ingredients, particularly mentioned above, the formulations of the present invention may include other agents conventional in the art having regard to the type of formulation in question, for example, those suitable for oral administration may include flavoring agents.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth. Unless defined otherwise, all technical and scientific terms used herein have the same meaning as commonly understood to one of ordinary skill in the art to which this invention belongs.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The above disclosure generally describes the present invention. A more complete understanding can be obtained by reference to the following examples. These examples are described solely for purposes of illustration and are not intended to limit the scope of the invention. Although specific terms have been employed herein, such terms are intended in a descriptive sense and not for purposes of limitations.

EXAMPLES

Example 1

Preparation and Use of S. aureus Lysate

Strains of S. aureus bacteria were deposited with the Czech Collection of Microorganisms (CCM) and have been assigned accession no. CCM 4992, CCM 4993, CCM 4994, CCM 4995, CCM 4996, CCM 4997, CCM 4998. The bacteriophage used were from the group deposited with the Deutsche Sammlung von Mikroorganismen and Zeilkulturen GmbH (DSM) and having accession nos. DSM 14614, DSM 14615, DSM 14616.

The bacteria, stored as a lyophilized culture were streaked onto trypton agar or a similar nutrient agar medium. After 24-48 h incubation at 37° C., 50 ml trypton medium was inoculated with the bacteria grown on the agar plate. The inoculated medium was incubated at 37° C. for 18-20 h and the volume added to 500 ml medium and incubated for 1-2 h (based on OD measured at 600 nm). The phage stock was then added and the mixture was allowed to sit at room temperature for 12-18 h. The resulting lysate was centrifuged for 1 h at 5,000 rpm, and filtered using filters with a pore size of 0.22 µm. The mixture was tested for sterility using blood agar and phage titration using a 2-layer agar technique.

Example 2

Screening of Bacterial Strains

Bacterial strains are screened for the most common antigenic pattern using immunogenic methods such as fluorescent antibody identification, FACS selection, ELISA, Western blots, SDS gel electrophoresis or by other detection methods known to those skilled in the art. Generally, the antigenic pattern is measured by SDS gel eletrophoresis. The components of the SPL are separated in a gel and silver-stained. The antigenic pattern is determined by the presence/absence of particular bands in the gel.

Cultures of the selected bacteria were then infected by the introduction of phage homologues. The combinations of phage and bacteria were screened for phage strains that resulted in quantitative lysis of bacteria in a given time and strains that exhibited the most common antigenic pattern through the above-mentioned methods. Combinations of bacterial and phage strains that exhibit reproducible results in lysis were selected. Combinations of one bacterial strain and different phages results in different antigenic combinations which can also be utilized. The selected bacterial and phage strains were preserved by lyophylization.

Example 3

Lyophilization

Phage are prepared by lysing the host bacteria resulting in $10^9$ to $10^{10}$ phage particles per ml.

0.5 ml of the phage containing bacterial lysate are placed in tubes to which 0.2 ml of skim milk has been added. The tubes are then covered with a sterile porous cover. The tubes are lyophilized using a cryodesiccator instrument such as 30P2 or EdwardsEF03 using primary desiccation for 4 h and secondary desiccation for 6 h. The tubes are then sealed.

Each batch of phage containing bacterial lysate is tested for viability by plating the contents of one tube on a layer of host bacteria and obtaining the titer from two-fold dilutions. The titer is compared to the starting titer prior to lyophilization.

Example 4

Stability Analysis

The stability of the lysate cultures is determined through stability assays which are repeated cultures and subcultures on plates and in liquid media. The stability studies are performed to select bacterial and phage strains that are most stable upon storage. The criteria measured by methods known to those skilled in the art are the measuring of antigenic pattern by SDS gel eletrophoresis; and phage virulence, excluding strains that become resistant to the phages used for infection. The cultures are also checked for reproducibility of antigenic patterns of lysates. Standardized inoculum of bacterial cells by the phages results in a very reproducible process of lysis. The resulting lysate is quantitatively and qualitatively analyzed by SDS gel electrophoresis.

Example 5

Preparation of Immunomodulators

Biological assays (e.g. blastic transformation, major antigenic proteins detected by Western blots, immunomodulation, etc.) are used to identify biologically active substances in the resultant lysates. A blastic transformation of peripheral lymphocytes is measured using individual fractions from SPL fractionated by chromatographic techniques. Activation markers or thymidine incorporation is used in the assay. Active fractions (those stimulating/inhibiting activation of peripheral lymphocytes) are further fractionated and used for isolation of a desired immunomodulator. One or more of these substances are then purified from one or more of the resultant lysates and identified and combinations are formed having the desired activities. Two or more of the resultant lysates identified are mixed together to yield the final polyclonal immunomodulator.

Example 6

Treatment with S. Aureus Lysates

Patients receive a subcutaneous dose 0.05 cc-0.2 cc (5 cc bottle) of the filtrate prepared as described in Example 5 into the antebrachium (forearm). The dose is dependent on the age, clinical and immunological status of the patient. In hypersensitive patients, the doses should be 0.02 cc-0.03 cc. This smaller dose is divided in half and applied into both antebrachiums, with the same amount administered at each repetition. Doses are administered every 3-5 days following the resolution of any prior local reaction. The dose are gradually increased in non-hypersensitive patients to 0.05 cc subcutaneously, according to individual reaction of the patient. In severe cases, the dose can be increased to 1.0 cc subcutaneous per dose. If the local reaction lasts longer then 4 days, the same dose should be repeated in the subsequent administration.

In pediatric applications, i.e. for children aged 3-10 years, the dosage is decreased by 50% from the above regime, or may be administered according to individualized reactions.

The length of the treatment is dependent on the clinical and immunological status of the patient. Generally the lysates are administered every 3-5 days for 3 months. This dosing regime can be repeated periodically as a booster.

In the case of milder infection or in pediatric indications the lysate can be administered as nasal drops. The dose is 4 drops in each nostril daily for four days and thereafter every other day. Different routes of administration may be combined.

Example 7

Stimulation of Metabolic Burst in Phagocytic Cells (Monocytes and Polymorphonuclear Leukocytes) in Human Blood In Vitro Samples of blood were collected and stored with heparin. The heparinized blood was used 2 h and 7 h after collection and the 100-microliter samples were incubated with SPL and other negative (no addition) and positive controls including a peptide, formyl-MetLeuPhe (FMLP) (physiological stimulator), phorbol-12-myristate-13-acetate (PMA; strong stimulator).

A bursatest kit (Orpegen Pharma) was used for detection of metabolic burst in monocytes and polymorphonuclear leukocytes, respectively. Cell sorter (FACStrak) was used to count number of positive cells and total cells.

TABLE 1

| Sample | Polymorphonuclear leukocytes (% of positive cells) | | Monocytes (% of positive cells) | |
|---|---|---|---|---|
| | 2-h sample | 7-h sample | 2-h sample | 7-h sample |
| Negative control | 9.7 | 19.4 | 13.9 | 18.1 |
| SPL | 38.2 | 61.7 | 31.3 | 40.2 |
| FMLP | 13.8 | 26.3 | 15.8 | 18.8 |
| PMA | 99.6 | 99.8 | 98.7 | 99.5 |

Staphyloccocal lysate (SPL) induced metabolic burst in both monocytes and polymorphonuclear leukocytes in blood samples treated 2 h and 7 h after collection. This treatment led to an increase of 2.5-3.2-fold in monocytes and 3.6-4.3-fold in polymorphonuclear leukocytes versus the control.

Example 8

Activation of Sub-Population of T Cells in Human Blood In Vitro

Heparinized blood was incubated for 6 h with SPL and other negative (no addition) and positive controls including a peptide formyl-MetLeuPhe (physiological stimulator), phorbol-12-myristate-13-acetate (PMA; strong stimulator), serum-opsonized Escherichia coli cells (E. coli-o) (gram-negative bacterium containing lipopolysaccharides), and phytohemaglutinin (PHA; T-cell stimulator). Using Fastimmune test and FACStrak with triple fluorescence, early activation (CD69+) and production of interpheron gamma (IFN-g) was measured in CD4+ T cells. Isotype controls were used to subtract background staining.

TABLE 2

| Sample | CD69+ (% of positive cells) | (CD69+) & (IFN-g+) (% of positive cells) | (IFN-g+) (% of positive cells) |
|---|---|---|---|
| Negative control | 0.56 | 0 | 0.02 |
| PMA | 76.04 | 3.09 | 0.04 |
| fMLP | 0.85 | 0 | 0 |
| PHA | 76.19 | 2.90 | 0.21 |
| E. coli-o | 10.12 | — | 0 |
| SPL-50 ul | 14.25 | 0.63 | 0.01 |
| SPL-100 ul | 17.11 | 0.86 | 0.01 |
| SPL-150 ul | 18.37 | 0.75 | 0.04 |

SPL induced earlier and greater activation (CD69+) of CD4+ T cells than fMLP or E. coli-o and the levels reached about 20% of those induced by mitogens PMA or PHA.

When cells producing IFN-γ were counted in the CD69+ subpopulation of CD4+ T lymphocytes stimulated with SPL, the levels were 30% of those stimulated with mitogens PMA or PHA.

E. coli-stimulated or fMLP-stimulated CD4+ T lymphocytes did not show any significant production of IFN-γ in the CD-69+ sub-population. In contrast, SPL-stimulated cells showed significant production of IFN-γ in the early-activated (CD69+) cells.

What is claimed is:

1. A method of treating a pathological condition or a microbial infection in a human or animal, comprising administering to a human or an animal a bacterial lysate derived from the infection of at least one non-pathogenic bacterial strain of Staphylococcus aureus with at least one bacteriophage, wherein the at least one bacterial strain is a Staphylococcus

*aureus* strain deposited with the Czech Collection of Microorganisms (CCM) having accession number CCM 4992 or 4993, or both strains 4992 and 4993; and the at least one bacteriophage is a bacteriophage deposited with the Deutsche Sammlung von Mikroorganismen and Zellkulturen GmBH (DSM) having accession number DSM 14614.

2. The method of claim 1, wherein the lysate further comprises a pharmaceutical excipient.

3. The method of claim 1, wherein the lysate further comprises an adjuvant.

4. The method of claim 1, wherein the pathological condition or microbial infection is chronic upper respiratory disease, wound infection, mastitis, osteomyelitis, endocarditis, skin polymicrobial infections, bronchial asthma, chronic sinusitis, cystic fibrosis or acne vulgaris.

5. The method of claim 1, wherein the lysate is administered subcutaneously, intradermally, intramuscularly, nasally, topically, or parenterally.

6. The method of claim 1, wherein the lysate is administered prophylactically.

7. The method of claim 1, wherein the lysate is administered more than one time.

8. The method of claim 1, wherein the lysate is administered more than one time by one or more than one administration route.

* * * * *